United States Patent
Pasini et al.

(10) Patent No.: US 9,988,363 B2
(45) Date of Patent: Jun. 5, 2018

(54) PROCESS FOR PREPARING ORGANIC ESTERS

(71) Applicant: ENI S.p.A., Rome (IT)

(72) Inventors: Thomas Pasini, Santarcangelo di Romagna (IT); Alberto Renato De Angelis, Legnano (IT)

(73) Assignee: ENI S.p.A., Rome (IT)

(*) Notice: Subject to any disclaimer, the term of this patent is extended or adjusted under 35 U.S.C. 154(b) by 0 days. days.

(21) Appl. No.: 15/507,460

(22) PCT Filed: Sep. 1, 2015

(86) PCT No.: PCT/IB2015/056632
§ 371 (c)(1),
(2) Date: Feb. 28, 2017

(87) PCT Pub. No.: WO2016/035009
PCT Pub. Date: Mar. 10, 2016

(65) Prior Publication Data
US 2017/0247347 A1    Aug. 31, 2017

(30) Foreign Application Priority Data
Sep. 2, 2014   (IT) .............. MI2014A1529

(51) Int. Cl.
C07D 307/02   (2006.01)
C07C 67/00    (2006.01)
C07D 307/68   (2006.01)
C07C 67/39    (2006.01)
B01J 21/10    (2006.01)

(52) U.S. Cl.
CPC .......... *C07D 307/68* (2013.01); *B01J 21/10* (2013.01); *C07C 67/39* (2013.01)

(58) Field of Classification Search
CPC ......... C07D 307/68; B01J 21/10; C07C 67/39
USPC ........................ 549/484; 560/238
See application file for complete search history.

(56) References Cited

U.S. PATENT DOCUMENTS

| 4,213,917 A | 7/1980 | Dolhyj et al. |
| 4,518,796 A | 5/1985 | Aoshima et al. |
| 4,877,898 A | 10/1989 | Paparizos et al. |

FOREIGN PATENT DOCUMENTS

| CN | 101376629 A | 3/2009 |
| DE | 10 2005 030 882 A1 | 1/2007 |

OTHER PUBLICATIONS

International Search Report and Written Opinion dated Oct. 30, 2015 in PCT/IB2015/056632.
Naoshi Mori, et al., "Facile oxidative conversion of alcohols to esters using molecular iodine" Tetrahedron Elsevier Science Publishers, vol. 61, No. 24, XP027861344, Jun. 13, 2005, pp. 5915-5925.
Mingting Xu, et al., "Isobutanol and Methanol Synthesis on Copper Catalysts Supported on Modified Magnesium Oxide" Journal of Catalysis, vol. 171, No. 1, XP004468791, 1997, pp. 130-147.

*Primary Examiner* — Taylor V Oh
(74) *Attorney, Agent, or Firm* — Oblon, McClelland, Maier & Neustadt, L.L.P.

(57) ABSTRACT

The present invention relates to a process for preparing an ester having formula R—COO—R' (I), wherein R represents a group selected from: (i) a linear or branched alkyl, containing from 1 to 20 carbon atoms, (ii) an aryl containing from 6 to 12 carbon atoms, (iii) a heterocycle with 4 to 12 carbon atoms containing at least one heteroatom selected from O, N, P and S, R' represents a linear or branched alkyl containing from 1 to 12 carbon atoms, said process comprising at least a phase of reacting a reaction mixture comprising at least one aldehyde having formula R—CHO (II), wherein R has the meanings defined above, and at least one alcohol having general formula R'—OH (III), wherein R' has the meanings defined above, in the presence of at least one solid basic catalyst, at a temperature within the range of 120° C.-300° C., obtaining said ester having formula (I).

17 Claims, No Drawings

PROCESS FOR PREPARING ORGANIC ESTERS

The present invention relates to a process for preparing organic esters that can be mainly used as fuel additives.

As is known, compounds belonging to the category of organic esters are widely used in various types of industry. Organic esters are used, for example, in the formulation of paints, food products and cosmetic products. Some organic esters, in particular, are also used as additives in fuels for the automotive field, for example, for reducing emissions of particulate generated during the combustion of fuels. Furthermore, when esters are obtained from renewable sources (for example from waste glycerine of processes for the production of biodiesel), they can be used as components in the formulation of so-called bio-fuels.

In the art, organic esters are mainly prepared through processes that comprise at least a first reaction step wherein an aldehyde is oxidized to the corresponding acid, followed by a second reaction step wherein said acid is esterified with an alcohol.

The esterification reaction typically proceeds slowly and incompletely, as an equilibrium state is established between the reagents (acid) and products (ester), with no substantial prevalence of the products with respect to the reagents.

This state of equilibrium can be unbalanced in favour of the esters, using suitable catalysts and by carrying out the reaction at a high temperature. In spite of this, in order to synthesize organic esters on an industrial scale under acceptable economic conditions, it is in fact necessary to also recycle the non-converted reagents, which complicates the synthesis process and its management.

In the two-step synthesis process, moreover, the carboxylic acid obtained in the first step must be isolated and purified before being able to be subjected to the esterification reaction in the second step. The separation and purification treatments however affects the plant and production costs of the esters.

A synthesis process of esters based on the Tishchenko reaction is also known in the state of the art. According to this reaction, an aldehyde is reacted in the presence of a basic catalyst. The basic catalyst can be an alkoxide or an aluminium alcoholate. The Tishchenko reaction is based on the disproportioning of the aldehyde with the subsequent formation of the ester. It is consequently only possible to obtain "symmetrical" esters with this reaction, having formula R—COO—R, i.e. esters having identical hydrocarbon groups R. The Tishchenko reaction is used industrially, for example, for producing the solvents ethyl acetate and isobutyl isobutyrate.

The objective of the present invention is to overcome the drawbacks of the known art.

In particular, a first objective of the present invention is to provide a process for the preparation of organic esters that is effective and easier to implement with respect to the processes of the known art.

A second objective of the present invention is to provide a process for the preparation of organic esters which avoids the separation and purification steps of reaction intermediates.

A further objective of the present invention is to provide a preparation process of organic esters which does not require recycling of the non-converted reagents.

In the light of these objectives and yet others that will appear more evident hereunder, a process is provided, in accordance with the present invention, for preparing an ester having formula R—COO—R' (I), wherein R represents a group selected from:

(i) a linear or branched alkyl, containing from 1 to 20 carbon atoms,
(ii) an aryl containing from 6 to 12 carbon atoms,
(iii) a heterocycle containing from 4 to 12 carbon atoms containing at least one heteroatom selected from O, N, P and S, R' represents a linear or branched alkyl containing from 1 to 12 carbon atoms, said process comprising at least a phase of reacting a reaction mixture comprising at least one aldehyde having formula R—CHO (II), wherein R has the meanings defined above, and at least one alcohol having general formula R'—OH (III), wherein R' has the meanings defined above, in the presence of at least one solid basic catalyst, at a temperature $T_H$ within the range of 120° C.-300° C., obtaining said ester having formula (I).

The Applicant has surprisingly found that esters having formula (I) can be obtained by reacting an aromatic or aliphatic aldehyde together with an alcohol in the presence of a solid basic catalyst.

The synthesis of the esters having formula (I) is thus advantageously obtained starting from an aldehyde and an alcohol in a single reaction step, avoiding the intermediate transformation of the aldehyde into the corresponding carboxylic acid and subsequent esterification with an alcohol. Furthermore, with the process according to the present invention, it is not necessary to separate and purify any reaction intermediate.

Furthermore, as the reaction yield is sufficiently high, the process according to the present invention can be carried out industrially also without recirculating the effluent at the outlet of the process containing the non-converted reagents.

A further advantage of the process according to the present invention with respect to processes based on the Tishchenko reaction lies in the fact that the esters that can be obtained are not symmetrical, i.e. they have formula R—COO—R', wherein R and R' can also be different from each other.

In a first embodiment of the present invention, the aldehydes having formula R—CHO (II) can be aliphatic aldehydes.

The aliphatic aldehydes are preferably selected from aldehydes having formula R—CHO (II) wherein R is a linear or branched $C_1$-$C_{20}$ alkyl, saturated or unsaturated. R is more preferably a $C_1$-$C_{10}$ alkyl and is even more preferably a $C_1$-$C_8$ alkyl. In a further preferred embodiment, R is a saturated linear alkyl.

Examples of preferred aliphatic aldehydes that can be used in the present invention are propionic aldehyde and acetic aldehyde.

In a second embodiment of the present invention, the aldehydes having formula R—CHO (II) are aromatic aldehydes.

The aromatic aldehydes are preferably selected from aldehydes having formula R—CHO (II) wherein R is a $C_6$-$C_{12}$ aryl, possibly substituted with at least one linear or branched $C_1$-$C_4$ alkyl, saturated or unsaturated.

Examples of preferred aromatic aldehydes that can be used for the purposes of the present invention are benzaldehyde (R=benzene) and toluic aldehyde (R=tolyl).

In a further embodiment of the present invention, the aromatic aldehydes are preferably selected from aldehydes having formula R—CHO (II) wherein R is a $C_4$-$C_{12}$ heterocycle, saturated or unsaturated, containing at least one heteroatom selected from O, N, P and S. Said heterocycle can be possibly substituted with at least one linear or branched $C_1$-$C_4$ alkyl, saturated or unsaturated.

An example of a heterocyclic aldehyde that can be used for the purposes of the present invention is furfuryl aldehyde (R=furfuryl).

Alcohols that can be used for the purposes of the present invention are alcohols having formula R'—OH (III), wherein R' is a linear or branched $C_1$-$C_{12}$ alkyl, saturated or unsaturated. R' is more preferably a $C_1$-$C_{10}$ alkyl and even more preferably a $C_1$-$C_8$ alkyl. In a further preferred embodiment, R is a saturated linear alkyl.

Said alcohols having formula (II) are preferably selected from methanol, ethanol, propanol and butanol; more preferably from methanol and ethanol.

In the process according to the present invention, the reaction mixture comprising the aldehyde having formula (I) and the alcohol having formula (II) is reacted in the presence of at least one solid basic catalyst.

The solid basic catalyst can be selected from catalysts commonly used for condensation reactions, such as, for example, the catalysts used for the aldol condensation reaction. Solid basic catalysts that can be used for the purposes of the present invention are described, for example, in C. Palomo, M. Oiarbide, J. M. Garcia, *The aldol addition reaction: an old transformation at constant rebirth*, Chem. Eur. J., 2002, 8, 36, and in Mukaiyama, *The direct aldol reaction, Organic Reactions*, New York, 1982, vol. 28, page 203.

Preferred solid basic catalysts that can be used, alone or mixed with each other, in the process according to the present invention are:

oxides of alkaline or alkaline-earth metals, preferably magnesium, calcium and lithium oxides;

hydrotalcites having general formula $M^{2+}{}_n M^{3+}{}_2 (OH)_{16} X.mH_2O$, wherein $M^{2+}$ is a bivalent metallic cation selected from $Mg^{2+}$, $Fe^{2+}$, $Ni^{2+}$, $Zn^{2+}$, $Cd^{2+}$, $Co^{2+}$, $M^{3+}$ is a trivalent metallic cation selected from $Al^{3+}$, $Fe^{3+}$, $Ga^{3+}$, $Cr^{3+}$, $Mn^{3+}$, $Co^{3+}$, X is an anion selected from $CO_3{}^{2-}$, $OH^-$ and $NO^{3-}$, n is an integer ranging from 4 to 10, m is an integer lower than or equal to 10;

zeolites prevalently or completely exchanged with one or more alkaline and/or alkaline-earth metals, such as sodium, potassium, rubidium, caesium. Preferred zeolites are Y zeolite, beta zeolite, and the zeolite ZSM-5;

fluorides of alkaline metals supported on a solid substrate; the fluorides are preferably selected from potassium fluoride, caesium fluoride and mixtures thereof; the solid substrates are preferably selected from alumina, silica and mixtures thereof, the substrate is more preferably alumina.

For effecting the process according to the present invention, the aldehyde and starting alcohol are mixed together to form a reaction mixture.

The reaction mixture can also contain organic solvents, such as dichloromethane, benzene or toluene. Said solvents, however, are not necessary when the aldehydes and alcohols are liquid.

When the aldehyde is in solid form, it can be reacted with the alcohol to form the ester according to the present invention, after having been previously dissolved in a solvent. The solvent is preferably an alcohol having formula (III). The solvent is more preferably the alcohol also used as second reagent in the synthesis process of the ester according to the present invention.

The relative concentrations of aldehyde and alcohol in the reaction mixture can vary within a wide range of values. The alcohol is preferably present in the reaction mixture in excess with respect to the aldehyde. The molar ratio alcohol:aldehyde in the reaction mixture is preferably selected within the range of 1:1 to 30:1, more preferably from 1.5:1 to 20:1.

The reaction mixture is treated thermally in the presence of a solid basic catalyst. The catalyst can be dispersed, for example, in the reaction mixture or the mixture can be put in contact with a fixed catalytic bed.

In a first preferred embodiment of the process according to the present invention, the reaction mixture comprising at least one aldehyde and at least one alcohol is reacted in the presence of at least one solid basic catalyst at a temperature equal to or higher than 120° C. and lower than or equal to 300° C.

The reaction mixture is maintained at the preselected temperature within the above range for a time selected from 15 minutes to 10 hours, preferably from 30 minutes to 8 hours.

The synthesis reaction of the ester is carried out at a pressure within the range of 1 atm-100 atm, preferably 40-60 atmospheres.

A preferred aspect of the present invention is to carry out the reaction at a temperature $T_H$ and/or $T_L$, wherein $T_L$ is defined hereunder, in an inert atmosphere (e.g. nitrogen), with a low oxygen content (e.g. lower than 0.5% v/v), to avoid secondary oxidation reactions of the aldehyde.

At the end of the reaction, the reaction mixture contains at least the ester having general formula (I) and possible reaction by-products. Said by-products typically consist of the alcohols formed starting from the aldehydes used as reagents.

The synthesis reaction of the process according to the present invention also leads to the formation of gaseous hydrogen, which can be advantageously separated from the reaction mixture and recovered for other uses.

In a second and more preferred embodiment, the process according to the present invention comprises an additional reaction step wherein the reaction mixture is reacted at a temperature $T_L$ higher than 50° C. and lower than 120° C.; said additional reaction step precedes the above reaction step at a temperature $T_H$ within the range of 120-300° C.

According to this second and more preferred embodiment, the reaction mixture is then reacted in the presence of at least one solid basic catalyst and at least a first temperature $T_L$ higher than 50° C. and lower than or equal to 120° C., and subsequently at at least a second temperature $T_H$ higher than 120 and lower than or equal to 300° C., again in the presence of a solid basic catalyst.

The reaction step at the temperature $T_H$ is advantageously effected immediately after the step at the temperature $T_L$, raising the temperature of the reaction mixture from the preselected value $T_L$ to the preselected value $T_H$.

When the process is carried out at at least two different temperatures $T_L$ and $T_H$, the reaction mixture is preferably maintained at the temperature $T_L$ for a time selected within the range of 10 minutes-10 hours, preferably 1-3 hours.

When the process is carried out at at least two different temperatures $T_L$ and $T_H$, the reaction mixture is preferably maintained at the temperature $T_H$ for a time selected within the range of 10 minutes-6 hours, preferably 1-2 hours.

When the process is carried out at at least two different temperatures $T_L$ and $T_H$, the reaction mixture is preferably maintained at a pressure within the range of 1-5 atmospheres, preferably 2-4 atmospheres.

When the process is carried out at at least two different temperatures $T_L$ and $T_H$, the reaction mixture is preferably maintained at a pressure within the range of 10-100 atmospheres, preferably 40-60 atmospheres.

The solid basic catalyst used in the reaction at the temperature $T_L$ is selected from the same catalysts that can be used for the reaction at the temperature $T_H$. The solid basic catalysts used in the reaction steps at the temperatures $T_H$ and $T_L$ can be the same or different from each other.

Although there is no intention of referring to any particular theory herein, it is believed that the formation reaction of the ester starting from a mixture of an aldehyde R—CHO and an alcohol R'—OH is obtained through the formation of a reaction intermediate consisting of a hemiacetal having formula RCOHOR' (IV) according to the following scheme 1 ("cat." indicates the presence of the solid basic catalyst):

Scheme 1

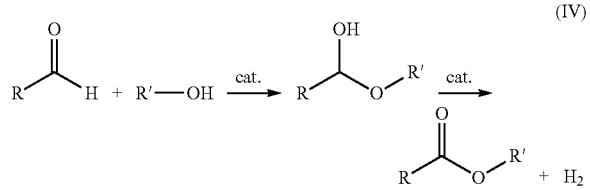

The formation of the hemiacetal having formula (IV) has been confirmed by some experimental tests carried out by the Applicant. In these tests, the synthesis process was effected by thermally treating the reaction mixture in the presence of the solid basic catalyst at two different temperatures $T_L$ and $T_H$, as described above, and analyzing the composition of the reaction mixture at the end of the reaction at the lower temperature $T_L$. The analysis of the mixture at the end of the reaction at the lower temperature $T_L$ shows the presence of the hemiacetal compound having formula (IV) in the reaction mixture. This compound is substantially absent, on the other hand, in the reaction mixture at the end of the reaction at the higher temperature $T_H$, where there is mainly the presence of the final ester and possible by-products. It can be observed that although the ester can be formed through a reaction intermediate such as the hemiacetal having formula (IV), the latter must not however be isolated from the reaction mixture.

In the process according to the present invention, the synthesis reaction is preferably effected at two different temperatures $T_L$ and $T_H$, so that at the lower temperature $T_L$, the reaction takes place between the aldehyde and the alcohol to give the formation of the corresponding hemiacetal, whereas at the higher temperature $T_H$, the oxidative dehydrogenation takes place, of the hemiacetal to the corresponding ester; as the second reaction is decisively endothermic, it requires a higher temperature to obtain a significant conversion degree of the intermediate hemiacetal to ester.

Operating at two different temperatures $T_L$ and $T_H$, the conversion degree of the reaction is maximized, at the same time optimizing the quantity of heat supplied to the reaction.

In the process according to the present invention, the conversion degree of the starting aldehyde (reaction yield) generally ranges from 50% to 100%, preferably from 75% to 100%; the selectivity of the reaction generally ranges from 20% to 100%, preferably from 50% to 100%.

The process according to the present invention can be carried out using devices and equipment known to skilled persons in the field.

The process can be carried out, for example, in continuous or batchwise.

The reaction can be carried out in one or more reactors, feeding the reagents in current or countercurrent. The reactors are preferably fixed-bed catalytic reactors.

The reaction is preferably carried out in a system consisting of two fixed-bed catalytic reactors, feeding the reagents in current or countercurrent, as said reactors are arranged in series and the two reactors operate at two different temperatures $T_L$ and $T_H$, with $T_L<T_H$.

Other reaction systems, however, can also be used, such as, for example, a system consisting of one or more CSTR reactors connected in series with each other.

At the end of the reaction, the final ester is separated from the reaction mixture, for example, by means of fractionated distillation or by solvent extraction.

The esters that can be obtained with the process according to the present invention can be destined for numerous uses. Said esters are preferably used as additives for fuels and in the preparation of cosmetic, food formulations, and paint products.

The following embodiment examples are provided for purely illustrative purposes of the present invention and should not be intended as limiting the protection scope defined by the enclosed claims.

EXAMPLE 1

A magnesium oxide catalyst was prepared as follows. A solution of $Mg(NO_3)_2$ 1 M was added dropwise to a solution of sodium carbonate 1 M maintained at a temperature of 50-60° C., under stirring. The total volumes of the two solutions used were the same. The pH of the final suspension of magnesium hydroxide was maintained at 9.5: in the case of deviation from said value, the pH was adjusted by the addition of a suitable quantity of nitric acid or sodium hydroxide.

At the end of the addition of $Mg(NO_3)_2$, the suspension was kept under stirring for 45 minutes, always at 60° C.

The suspension was then filtered and the product collected was washed with distilled water, in a ratio equal to 330 ml of water per gram of product collected.

The magnesium hydroxide thus obtained was dried at 120° C. for 4 hours.

The magnesium hydroxide was then calcined at 450° C. for 5 hours in air, transforming it into the corresponding oxide (surface area equal to 150 m²/g).

EXAMPLE 2

60 ml of anhydrous methanol were charged into an autoclave having a capacity of 150 ml. 1 g of furfural and 2 g of magnesium oxide prepared as described in Example 1, were added to this.

The autoclave was closed and purged with nitrogen to eliminate the air present in its interior. The reaction mixture was heated in the presence of the catalyst to two different temperatures ($T_L$=100° C. and $T_H$=160° C.) under the following conditions.

The reaction mixture was heated to 100° C. for 1 hour under stirring (1,000 rpm). The temperature was then raised from 100° C. to 160° C. and the mixture was heated to this temperature for 2 hours in autogenous pressure, equal to 60 bar, under stirring (1,000 rpm).

The autoclave containing the reaction mixture was then cooled to room temperature and then opened. The reaction mixture extracted from the autoclave was filtered to separate the magnesium oxide. The mixture was subsequently subjected to HPLC analysis to determine its composition.

The analyses indicated a conversion of furfural equal to 50% and a selectivity to the methyl furfurate ester equal to 80%, the remaining 20% of the converted furfural consisting of furfuryl alcohol.

EXAMPLE 3

A reaction mixture prepared according to Example 2 and containing anhydrous methanol, furfural and magnesium oxide (prepared according to what is described in Example 1) was subjected to two heating steps to temperatures $T_L=100°$ C. and $T_H=160°$ C. under the following conditions.

The reaction mixture was heated to 100° C. for 2 hours under stirring (1,000 rpm). The temperature was then raised from 100° C. to 160° C. and the mixture was heated to this temperature for 3 hours in autogenous pressure, equal to 60 bar, under stirring (1,000 rpm).

The autoclave containing the reaction mixture was then cooled to room temperature and then opened. The reaction mixture extracted from the autoclave was filtered to separate the magnesium oxide. The mixture was subsequently subjected to HPLC analysis to determine its composition.

The analyses indicated a conversion of furfural equal to 75% and a selectivity to the methyl furfurate ester equal to 90%, the remaining 10% of the converted furfural consisting of furfuryl alcohol.

EXAMPLE 4

A reaction mixture prepared according to Example 2 and containing anhydrous methanol, furfural and magnesium oxide (prepared according to what is described in Example 1) was subjected to two heating steps at temperatures $T_L=100°$ C. and $T_H=200°$ C. under the following conditions.

The reaction mixture was heated to 100° C. for 2 hours under stirring (1,000 rpm). The temperature was then raised from 100° C. to 200° C. and the mixture was heated to this temperature for 3 hours in autogenous pressure, equal to 85 bar, under stirring (1,000 rpm).

The autoclave containing the reaction mixture was then cooled to room temperature and then opened. The reaction mixture extracted from the autoclave was filtered to separate the magnesium oxide. The mixture was subsequently subjected to HPLC analysis to determine its composition.

The analyses indicated a conversion of furfural equal to 100% and a selectivity to the methyl furfurate ester equal to 80%, the remaining 20% of the converted furfural consisting of furfuryl alcohol.

EXAMPLE 5

60 ml of anhydrous ethanol were charged into an autoclave having a capacity of 150 ml. 2 g of benzaldehyde and 2.5 g of magnesium oxide prepared according to what is described in Example 1, were added to this.

The autoclave was closed and purged with nitrogen to eliminate the air present in its interior. The reaction mixture was heated in the presence of the catalyst to two different temperatures ($T_L=100°$ C. and $T_H=160°$ C.) under the following conditions.

The reaction mixture was heated to 100° C. for 1 hour under stirring (1,000 rpm). The temperature was then raised from 100° C. to 160° C. and the mixture was heated to this temperature for 2 hours in autogenous pressure, equal to 60 bar, under stirring (1,000 rpm).

The autoclave containing the reaction mixture was then cooled to room temperature and then opened. The reaction mixture extracted from the autoclave was filtered to separate the magnesium oxide. The mixture was subsequently subjected to HPLC analysis to determine its composition.

The analyses indicated a conversion of benzaldehyde equal to 70% and a selectivity to the ethyl benzoate ester equal to 85%, the remaining 15% of the converted benzaldehyde consisting of benzylic alcohol.

The invention claimed is:

1. A process for preparing an ester of formula (I):

the process comprising:
reacting a reaction mixture comprising at least one aldehyde having formula (II): R—CHO (II) and at least one alcohol having formula (III): R'—OH (III) in the presence of at least one solid basic catalyst, at a temperature $T_H$ of higher than or equal to 120° C. and lower than 300° C., in an inert atmosphere, to obtain the ester of the formula (I) with a selectivity ranging from 20 to 100% with respect to the at least one aldehyde having the formula (II),
wherein
in the formulae (I), (II), and (III), R represents a group selected from the group consisting of: i) a linear or branched $C_1$-$C_{20}$ alkyl, (ii) a $C_6$-$C_{12}$ aryl, and (iii) a heterocycle having 4 to 12 carbon atoms and at least one heteroatom selected from the group consisting of O, N, P and S, and R' represents a linear or branched $C_1$-$C_{12}$ alkyl; and
the at least one solid basic catalyst is selected from the group consisting of
an oxide of one or more alkaline or alkaline earth metals,
a hydrotalcite of formula $(M^{2+})_n(M^{3+})_2(OH)_{16}$ X.m$H_2O$, where $M^{2+}$ is a bivalent metallic cation selected from the group consisting of $Mg^{2+}$, $Fe^{2+}$, $Ni^{2+}$, $Zn^{2+}$, $Cd^{2+}$, and $Co^{2+}$, $M^{3+}$ is a trivalent metallic cation selected from the group consisting of $Al^{3+}$, $Fe^{3+}$, $Ga^{3+}$, $Cr^{3+}$, $Mn^{3+}$, and $Co^{3+}$, X is an anion selected from the group consisting of $CO_3^{2-}$, $OH^-$, and $NO_3^-$, n is an integer ranging from 4 to 10, and m is an integer lower than or equal to 10,
a zeolite prevalently or completely exchanged with one or more alkaline and/or alkaline-earth metals, and
a fluoride of an alkaline metal supported on a solid substrate of alumina, silica, or a mixture thereof.

2. The process according to claim 1, wherein R is a linear $C_1$-$C_{10}$ alkyl.

3. The process according to claim 1, wherein R is a $C_6$-$C_{12}$ aryl, optionally substituted with at least a linear or branched $C_1$-$C_4$ alkyl, saturated or unsaturated.

4. The process according to claim 1, wherein R' is a $C_1$-$C_{10}$ alkyl.

5. The process according to claim 4, wherein the reacting at the temperature $T_H$ has a duration ranging from 15 minutes to 10 hours.

6. The process according to claim 1, wherein the reacting at the temperature $T_H$ is carried out at a pressure ranging from 1 atm to 100 atm.

7. The process according to claim 1, wherein a molar ratio between the alcohol and the aldehyde in the reaction mixture ranges from 1:1 to 30:1.

8. The process according to claim 1, further comprising:
before the reacting at the temperature $T_H$, reacting the reaction mixture in the presence of the at least one solid basic catalyst at a temperature $T_L$ higher than 50° C. and lower than or equal to 120° C., wherein the temperature $T_L$ is lower than the temperature $T_H$.

9. The process according to claim 8, wherein the reaction mixture is kept at the temperature $T_L$ for a time ranging from 10 minutes to 10 hours.

10. The process according to claim 8, wherein the reaction mixture is kept at the temperature $T_H$ for a time ranging from 10 minutes to 6 hours.

11. The process according to claim 1, wherein R is a linear $C_1$-$C_8$ alkyl.

12. The process according to claim 1, wherein R' is a linear $C_1$-$C_8$ alkyl.

13. The process according to claim 4, wherein the reacting at the temperature $T_H$ has a duration ranging from 30 minutes to 8 hours.

14. The process according to claim 1, wherein the reacting at the temperature $T_H$ is carried out at a pressure ranging from 40 to 60 atm.

15. The process according to claim 1, wherein a molar ratio between the alcohol and the aldehyde in the reaction mixture ranges from 1.5:1 to 20:1.

16. The process according to claim 8, wherein the reaction mixture is kept at the temperature $T_L$ for a time ranging from 1 to 3 hours.

17. The process according to claim 8, wherein the reaction mixture is kept at the temperature $T_H$ for a time ranging from 1 to 2 hours.

\* \* \* \* \*